United States Patent
Faltynowicz et al.

(10) Patent No.: US 11,884,745 B2
(45) Date of Patent: Jan. 30, 2024

(54) METHOD OF REMOVING LIPOPEPTIDES FROM SOLUTIONS AND CHANGING THEIR STRUCTURE

(71) Applicant: INVENTIONBIO SPOLKA Z OGRANICZONA ODPOWIEDZIALNOSCIA, Bydgoszcz (PL)

(72) Inventors: Hanna Faltynowicz, Wisznia Mala (PL); Marek Kulazynski, Wroclaw (PL); Marcin Lukaszewicz, Wroclaw (PL)

(73) Assignee: INVENTIONBIO SP. Z O. O., Bydgoszcz (PL)

( * ) Notice: Subject to any disclaimer, the term of this patent is extended or adjusted under 35 U.S.C. 154(b) by 0 days.

(21) Appl. No.: 17/059,403

(22) PCT Filed: May 30, 2019

(86) PCT No.: PCT/IB2019/054480
§ 371 (c)(1),
(2) Date: Nov. 27, 2020

(87) PCT Pub. No.: WO2019/229690
PCT Pub. Date: Dec. 5, 2019

(65) Prior Publication Data
US 2021/0214393 A1 Jul. 15, 2021

(30) Foreign Application Priority Data
May 30, 2018 (PL) .......................... 425775

(51) Int. Cl.
*C07K 7/06* (2006.01)
(52) U.S. Cl.
CPC ..................... *C07K 7/06* (2013.01)
(58) Field of Classification Search
None
See application file for complete search history.

(56) References Cited

PUBLICATIONS

Liu et al. (Biochemical Engineering Journal 35 (2007) 333-340) (Year: 2007).*
Bernal et al. (Journal of Carbon Research 4(4):62) (Year: 2018).*
Merck (downloaded on Oct. 28, 2021 from URL :< Charcoal activated CAS 7440-44-0 | 102514 (emdmillipore.com)) (Year: 2021).*
Ao et al. (Renewable and Sustainable Energy Reviews 92 (2018) 958-979) (Year: 2018).*
Stone et al. (Langmuir. Jul. 15, 2014;30(27):8046-55) (Year: 2014).*
Norit (Safety data sheet, May 11, 2016) (Year: 2016).*
Crittenden et al. (Adsorption 11: 537-541, 2005) (Year: 2005).*
Dufour S et al, "Hemolytic activity of new linear surfactin analogs in relation to their physico-chemical properties", Oct. 30, 2005 (Oct. 30, 2005), vol. 1726, No. 1, p. 87-95, XP027639595, ISSN:0304-4165.
Morikawa A M et al, "A study on the structure-function relationship of lipopeptide biosurfactants", Biochimica Et Biophysica Acta (BBA)—Molecular and Cell Biology of Lipids, Elsevier, Amsterdam, NL, vol. 1488, No. 3, Nov. 15, 2000 (Nov. 15, 2000), p. 211-218, XP004277436, DOI: 10.1016/S1388-1981(00)00124-4 external link, ISSN:1388-1981, p. 213, paragraph 2.4.
Kirti V. Dubey et al, "Adsorption-;Desorption Process Using Wood-Based Activated Carbon for Recovery of Biosurfactant from Fermented Distillery Wastewater", Biotechnology Progress, vol. 21, No. 3, Sep. 5, 2005 (Sep. 5, 2005), p. 860-867, XP055650531, DOI: 10.1021/bp040012e external link, ISSN:8756-7938, the whole document.
Mnif Inès et al, "Lipopeptide surfactants: Production, recovery and pore forming capacity", Peptides, vol. 71, Sep. 1, 2015 (Sep. 1, 2015), p. 100-112, XP055580317, DOI: 10.1016/j.peptides.2015. 07.006 external link, ISSN:0196-9781, p. 104, paragraph 2., Table 2.
Faltynowicz Hanna et al, "Hydrolysis of surfactin over activated carbon", Apr. 3, 2019 (Apr. 3, 2019), vol. 93, XP085903735, DOI: 10.1016/J.BIOORG.2019.03.070 external link, ISSN:0045-2068, the whole document.

* cited by examiner

*Primary Examiner* — Sergio Coffa
(74) *Attorney, Agent, or Firm* — Craft Chu PLLC; Andrew W. Chu

(57) ABSTRACT

The present invention is a method for removing lipopeptides from solutions and changing their structure from cyclic to linear. The lipopeptide capture and sequestration takes place from solutions containing water through sorption. In the case of cyclic lipopeptides, in which the peptide ring is closed by a lactone bond, sorption is additionally associated with hydrolysis reactions occurring on the surface of active carbon, leading to linearization as a result of breaking the lactone bond.

9 Claims, No Drawings

Specification includes a Sequence Listing.

SEQUENCE LISTING

<160> NUMBER OF SEQ ID NOS: 19

<210> SEQ ID NO 1
<211> LENGTH: 7
<212> TYPE: PRT
<213> ORGANISM: Unknown
<220> FEATURE:
<223> OTHER INFORMATION: linear analogues of surfactin

```
<400> SEQUENCE: 1

Glu Leu Leu Val Asp Leu Leu
1               5

<210> SEQ ID NO 2
<211> LENGTH: 7
<212> TYPE: PRT
<213> ORGANISM: Unknown
<220> FEATURE:
<223> OTHER INFORMATION: linear analogues of surfactin

<400> SEQUENCE: 2

Glu Leu Leu Val Asp Leu Val
1               5

<210> SEQ ID NO 3
<211> LENGTH: 7
<212> TYPE: PRT
<213> ORGANISM: Unknown
<220> FEATURE:
<223> OTHER INFORMATION: linear analogues of surfactin

<400> SEQUENCE: 3

Glu Leu Leu Val Asp Leu Ile
1               5

<210> SEQ ID NO 4
<211> LENGTH: 7
<212> TYPE: PRT
<213> ORGANISM: Unknown
<220> FEATURE:
<223> OTHER INFORMATION: linear analogues of surfactin

<400> SEQUENCE: 4

Glu Leu Leu Leu Asp Leu Ile
1               5

<210> SEQ ID NO 5
<211> LENGTH: 7
<212> TYPE: PRT
<213> ORGANISM: Unknown
<220> FEATURE:
<223> OTHER INFORMATION: linear analogues of surfactin

<400> SEQUENCE: 5

Glu Leu Leu Leu Asp Leu Val
1               5

<210> SEQ ID NO 6
<211> LENGTH: 7
<212> TYPE: PRT
<213> ORGANISM: Unknown
<220> FEATURE:
<223> OTHER INFORMATION: linear analogues of surfactin

<400> SEQUENCE: 6

Glu Leu Leu Ala Asp Leu Leu
1               5

<210> SEQ ID NO 7
<211> LENGTH: 7
<212> TYPE: PRT
<213> ORGANISM: Unknown
<220> FEATURE:
<223> OTHER INFORMATION: linear analogues of surfactin
```

```
<400> SEQUENCE: 7

Glu Leu Leu Leu Asp Leu Leu
1               5

<210> SEQ ID NO 8
<211> LENGTH: 7
<212> TYPE: PRT
<213> ORGANISM: Unknown
<220> FEATURE:
<223> OTHER INFORMATION: linear analogues of surfactin

<400> SEQUENCE: 8

Glu Leu Leu Ile Asp Leu Leu
1               5

<210> SEQ ID NO 9
<211> LENGTH: 7
<212> TYPE: PRT
<213> ORGANISM: Unknown
<220> FEATURE:
<223> OTHER INFORMATION: linear analogues of surfactin

<400> SEQUENCE: 9

Glu Leu Leu Ile Asp Leu Ile
1               5

<210> SEQ ID NO 10
<211> LENGTH: 7
<212> TYPE: PRT
<213> ORGANISM: Unknown
<220> FEATURE:
<223> OTHER INFORMATION: linear analogues of surfactin

<400> SEQUENCE: 10

Glu Ile Leu Ile Asp Leu Ile
1               5

<210> SEQ ID NO 11
<211> LENGTH: 7
<212> TYPE: PRT
<213> ORGANISM: Unknown
<220> FEATURE:
<223> OTHER INFORMATION: linear analogues of surfactin

<400> SEQUENCE: 11

Glu Val Leu Val Asp Leu Val
1               5

<210> SEQ ID NO 12
<211> LENGTH: 7
<212> TYPE: PRT
<213> ORGANISM: Unknown
<220> FEATURE:
<223> OTHER INFORMATION: linear analogues of surfactin

<400> SEQUENCE: 12

Glu Ile Leu Val Asp Leu Val
1               5

<210> SEQ ID NO 13
<211> LENGTH: 7
<212> TYPE: PRT
<213> ORGANISM: Unknown
<220> FEATURE:
<223> OTHER INFORMATION: linear analogues of surfactin

<400> SEQUENCE: 13
```

```
Glu Ile Leu Val Asp Leu Ile
1               5

<210> SEQ ID NO 14
<211> LENGTH: 7
<212> TYPE: PRT
<213> ORGANISM: Unknown
<220> FEATURE:
<223> OTHER INFORMATION: linear analogues of surfactin

<400> SEQUENCE: 14

Gln Leu Leu Val Asp Leu Leu
1               5

<210> SEQ ID NO 15
<211> LENGTH: 7
<212> TYPE: PRT
<213> ORGANISM: Unknown
<220> FEATURE:
<223> OTHER INFORMATION: linear analogues of surfactin

<400> SEQUENCE: 15

Gln Leu Leu Val Asp Leu Val
1               5

<210> SEQ ID NO 16
<211> LENGTH: 7
<212> TYPE: PRT
<213> ORGANISM: Unknown
<220> FEATURE:
<223> OTHER INFORMATION: linear analogues of surfactin

<400> SEQUENCE: 16

Gln Leu Leu Val Asp Leu Ile
1               5

<210> SEQ ID NO 17
<211> LENGTH: 7
<212> TYPE: PRT
<213> ORGANISM: Unknown
<220> FEATURE:
<223> OTHER INFORMATION: linear analogues of surfactin

<400> SEQUENCE: 17

Gln Leu Leu Ala Asp Leu Leu
1               5

<210> SEQ ID NO 18
<211> LENGTH: 7
<212> TYPE: PRT
<213> ORGANISM: Unknown
<220> FEATURE:
<223> OTHER INFORMATION: linear analogues of surfactin

<400> SEQUENCE: 18

Gln Leu Leu Ala Asp Leu Val
1               5

<210> SEQ ID NO 19
<211> LENGTH: 7
<212> TYPE: PRT
<213> ORGANISM: Unknown
<220> FEATURE:
<223> OTHER INFORMATION: linear analogues of surfactin
```

```
<400> SEQUENCE: 19

Gln Leu Leu Ala Asp Leu Ile
1               5
```

METHOD OF REMOVING LIPOPEPTIDES FROM SOLUTIONS AND CHANGING THEIR STRUCTURE

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The subject matter of the invention is the method of removing lipopeptides from solutions and changing their structure.

2. Description of Related Art Including Information Disclosed Under 37 CFR 1.97 and 37 CFR 1.98

Biosurfactants are surfactants produced by microorganisms or obtained by biotransformation. They are biodegradable, less toxic and more resistant to extreme environmental conditions than their synthetic analogues, while maintaining an excellent ability to reduce surface tension at the phase boundary.

Lipopeptides are a group of biosurfactants whose molecules are composed of a cyclic peptide and a β-hydroxy fatty acid chain attached by an ester (lactone) bond. The best known lipopeptide is surfactin, produced by various strains of the genus *Bacillus*. It is available in the form of a series of homologues, which differ in the length of the carbon chain, 12-17 atoms of C, as described in P. Biniarz and M. Łukaszewicz, "Direct quantification of lipopeptide biosurfactants in biological samples via HPLC and UPLC-MS requires sample modification with an organic solvent", Appl. Microbiol. Biotechnol., Vol. 101, 15 No. 11, pp. 4747-4759, 2017, or even 18 atoms of C, as reported by S. Dufour, M. Deleu, K. Nott, B. Wathelet, et al., Hemolytic activity of new linear surfactin analogs in relation to their physico-chemical properties. Biochim. Biophys. Acta-Gen. Subj. 2005, 1726, 87-95, or in the composition or sequence of amino acids in the peptide ring.

Surfactin can be hydrolysed under the influence of various factors, leading to formation of new biosurfactants with different properties. The lactone bond, or one of the peptide bonds, is hydrolysed, which results in opening of the cyclic peptide and formation of linear analogues of surfactin.

There are known cases of hydrolysis occurring in the alkaline route, where saponification of the ester bond occurs under the influence of sodium hydroxide (NaOH) in methanol, as described in patent application US20060166869, or under the influence of sodium methanolate in methanol, as reported in T. Imura, S. Ikeda, K. Aburai, T. Taira and D. Kitamoto, "Interdigitated Lamella and Bicontinuous Cubic Phases Formation from Natural Cyclic Surfactin and Its Linear Derivative", J. Oleo Sci., Vol. 62, No. 7, pp. 499-503, 2013, or an aqueous solution of sodium or ammonium hydroxide, as specified in patent JPH0892279.

There are known cases of acidic hydrolysis, as described in patent JPH0892279. It takes place as a result of the hydrochloric acid action on cyclic surfactin.

Enzymatic hydrolysis, induced by enzymes secreted by microorganisms, is also known. *Streptomyces* sp. Mgl. strain produces an enzyme, surfactin hydrolase, which also causes hydrolysis of lactone bonds, as reported in B. C. Hoefler, K. V. Gorzelnik, J. Y. Yang, N. Hendricks, P. C. Dorrestein and P. D. Straight, "Enzymatic resistance to the lipopeptide surfactin as identified through imaging mass spectrometry of bacterial competition," Proc. Natl. Acad. Sci., Vol. 109, No. 32, pp. 13082-13087, 2012. In turn, V8 endoprotease, obtained from *Staphylococcus aureus*, causes hydrolysis of the peptide bond between glutamic acid (L-GluI) and leucine (L-Leu2), as described in I. Grangemard, J. Wallach and F. Peypoux, "Evidence of surfactin hydrolysis by a bacterial endoprotease", Biotechnol. Lett., Vol. 21, No. 3, pp. 241-244, 1999). There are also known cases of enzymatic hydrolysis of other lipopeptide compounds, e.g. the antibiotic daptomycin. The publication V. M. D'Costa et al., "Inactivation of the lipopeptide antibiotic daptomycin by hydrolytic mechanisms", Antimicrob. Agents Chemother., Vol. 56, No. 2, pp. 757-764, 2012, reports on a study of its biodegradability by 60 daptomycin-resistant Actinomycetales, 44% of which caused hydrolysis, and 29% deacylation of daptomycin.

Linear lipopeptides can also be produced directly by microorganisms. Three lipopeptides produced by *Bacillus subtilis* KCTC 1241 IBP strain are the subject of patent application KR20180003520A H. J. Shin, F. S. Tareq, HS. Lee, J. S. Lee Y. J. Lee, M. A. Lee "Gageostatins lipotetrapeptides produced from a marine-derived *Bacillus subtilis* having antimicrobial activity". They have the same composition of amino acids in the peptide part as surfactin, but with a different chiral configuration 60 (LLLDLLL compared to LLDLLDL in surfactin). There is also a possibility of genetic modification of microorganisms producing cyclic lipopeptides in their natural state. However, no linear surfactin analogues were obtained in this way, but only lipopeptides with shorter amino acid sequences (De Ferra, F., Rodriguez, F., Tortora, O., Tosi, C., Grandi, G., Engineering of peptide synthetases. Key role of the thioesterase-like domain for efficient production of recombinant peptides. *J. Biol. Chem.* 1997, 272, 25304-25309, Stachelhaus, T., Schneider, A., Marahiel, M., Rational design of peptide antibiotics by targeted replacement of bacterial and fungal domains. *Science* 1995, 269, 69-72).

In the case of enzymatic hydrolysis of peptide bond, its efficiency was up to 14%, while enzymatic hydrolysis of the lactone bond allowed to obtain 95% conversion of cyclic to linear surfactin. Alkaline chemical hydrolysis of the lactone bond led to a final product with 97% efficiency, while for acid hydrolysis efficiency was only 56%. However, chemical hydrolysis requires the use of toxic (methanol) and corrosive (NaOH, $NH_3$, $H_2O$ or HCl) compounds, which makes this process less environmentally friendly.

BRIEF SUMMARY OF THE INVENTION

The aim of the solution according to the invention is to produce a high purity product. Impurities in the form of the cyclic forms of lipopeptides are minimal and at the same time the use of environmentally unfriendly chemicals during hydrolysis is reduced.

The method according to the invention is based on the fact that lipopeptide capture and sequestration takes place from solutions containing water through sorption, and in the case of cyclic lipopeptides, in which the peptide ring is closed by a lactone bond, sorption is additionally associated with hydrolysis reactions occurring on the surface of active carbon, leading to linearisation as a result of breaking the lactone bond.

Preferably, the process of adsorption and/or desorption on activated carbon should be carried out using microwaves, magnetic field or electric current.

Preferably, the process should be carried out in a flow or in a stationary system.

Preferably, the activated carbon should be in the form of granulate, powder, or monoliths.

Preferably, the activated carbon should have a surface area above 600 $m^2/g$, and pH of its aqueous suspension should be above 6.

Preferably, linear lipopeptides should be separated using known methods.

Preferably, the structures of linear lipopeptides obtained in accordance with the method should have the following chemical formulae:

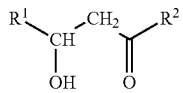

$R^1$—alkyl group with the number of C atoms >4 and linear, iso-, or anteiso-configuration,
$R^2$—a peptide terminated with a C-end of any sequence of amino acids and with a length of 4 to 12 amino acids.

BRIEF DESCRIPTION OF THE SEVERAL VIEWS OF THE DRAWINGS

None.

DETAILED DESCRIPTION OF THE INVENTION

An advantage of the solution is the hydrolysis of surfactin on active carbon as a catalyst is an environment-friendly process. In addition, activated carbon is an easily available natural product. It can be used as a reusable catalyst, and after use it can be easily and cheaply regenerated, e.g. by thermal treatment. An important advantage is the hydrolysis on activated carbon minimises use of environmentally unfriendly chemicals such as methanol, alkalis, or acids. In this case, hydrolysis is carried out in an aqueous solution. In this way, it is also possible to obtain a high purity product that is very little contaminated with cyclic forms of surfactin. The products obtained with an efficiency of up to 95% are fully biodegradable.

Example 1

From a post-fermentation solution containing a lipopeptide mixture with a dominant surfactin content, surfactin is released using a known method. 100 ml of the resulting 0.8 mg/ml aqueous solution of surfactin (a cyclic lipopeptide) is placed in a 250 ml conical flask. Then 1 gram of activated carbon with a particle size of 0.2 to 1 mm and a pore area of 650 $m^2/g$ and a pH of its aqueous suspension of 8.5 is added. The suspension is mixed using a shaker for 72 hours at 20° C. After this time, the solution is separated from activated carbon by filtration and centrifugation. The adsorbed surfactin (a portion of cyclic lipopeptides as adsorbed cyclic lipopeptides) remains on the activated carbon in the amount of 5% initially introduced into the solution. The remaining part of surfactin (another portion of cyclic lipopeptides) reacts on the surface of active carbon, forming surfactin hydrolysate (linear lipopeptides) with a linear structure represented by formulae (I) and (II).

(SEQ. ID. NO. 1)

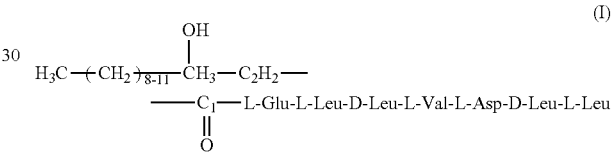

(SEQ. ID. NO. 1)

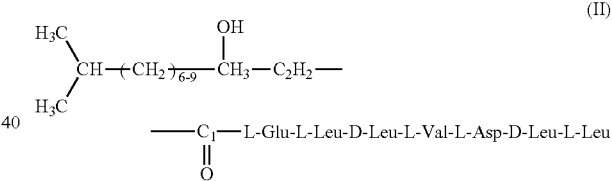

FIG. 1 Formulae of linear analogues of surfactin with amino acid sequences L-Glu-L-Leu-D-Leu-L-Val-L-Asp-D-Leu-L-Leu (SEQ. ID. NO. 1), in which the β-hydroxy fatty acid chain is composed of 12-15 atoms of C and which has a linear (I) or iso- (II) configuration.

Example 2

As in example 1, except that the concentration of the aqueous solution of surfactin is 2 mg/ml. Subsequently 3 grams of activated carbon with a particle size ranging from 0.1 to 0.2 mm and an internal surface area of 750 $m^2/g$ and a pH of 9 in aqueous suspension are introduced. The suspension is mixed using a shaker for 72 hours at 25° C. After this time, the solution is separated from activated carbon by filtration and centrifugation. Surfactin is adsorbed on active carbon in the amount of 3% initially introduced into the solution. The remaining part of surfactin reacts on the surface of carbon to form surfactin hydrolysate with a linear structure. A mixture of linear products is separated by preparative liquid chromatography into analogues differing in length of the alkyl chain, whose structure is shown in formula (III).

(SEQ. ID. NO. 1)

(III)

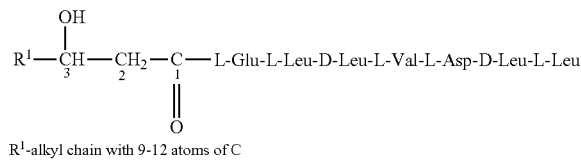

R¹-alkyl chain with 9-12 atoms of C

FIG. 2 Formula of a linear analogue of surfactin with an amino acid sequence L-Glu-L-Leu-D-Leu-L-Val-L-Asp-D-Leu-L-Leu (SEQ. ID. NO. 1), in which the β-hydroxy fatty acid chain is composed of 12-15 atoms of C, and which has a linear, iso- or anteiso-configuration.

Example 3

As in Example 1, except that the surfactin solution is applied to the column. The column is filled with 20 grams of activated carbon in the form of a monolith with a mesh size of 0.5×0.5 mm, wall thickness of 0.5 mm, pore area of 750 m²/g, and pH value of 9 in the aqueous suspension. At 25° C., using a peristaltic pump, 2000 ml/h of a 2 mg/ml surfactin solution in water is introduced from above. After passing through the active carbon bed, the solution is directed to a handling tank from which it is drawn using a pump to carry out the process in a flow system. The process is carried out for 48 hours. Surfactin is adsorbed on active carbon in the amount of 10% initially introduced into the solution. The remaining part of surfactin reacts on the surface of active carbon to form surfactin hydrolysates with a linear structure, presented in formulae (IV)-(VI), which remain in the circulating solution. Carbon can be used several times in the process. Carbon can be regenerated inside or outside the column.

FIG. 3 Formulae of the linear analogues of surfactin with an amino acid sequence L-Glu-L-Leu-D-Leu-L-Val-L-Asp-D-Leu-L-Leu (SEQ. ID. NO. 1), in which the β-hydroxy fatty acid chain is composed of 7-9 atoms of C and has a linear (IV), iso- (V) or anteiso- (VI) configuration.

Example 4

As in Example 1, except that the surfactin solution is applied to the column. The column is filled with 20 grams of activated carbon in the form of a monolith with a mesh size of 0.5×0.5 mm, wall thickness of 0.5 mm, internal surface area of 750 m²/g, and pH value of 9 in aqueous suspension. The monolith is connected to electric current during the flow of the solution. At 25° C., using a peristaltic pump, 2000 ml/h of a 2 mg/ml surfactin solution in water is introduced from above. After passing through the active carbon bed, the solution is directed to a handling tank from which it is drawn using a pump to carry out the process in a flow system. The process is carried out for 48 hours. Surfactin is absorbed on active carbon in the amount of 15% initially introduced into the solution. The remaining part of surfactin reacts on the surface of active carbon to form surfactin hydrolysates with a linear structure, presented in formulae (VII)-(IX), which remain in the circulation solution. Carbon can be used several times in the process.

(SEQ. ID. NO. 1)

(IV)

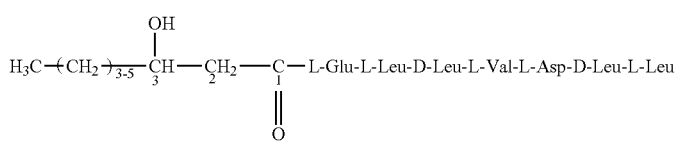

(SEQ. ID. NO. 1)

(V)

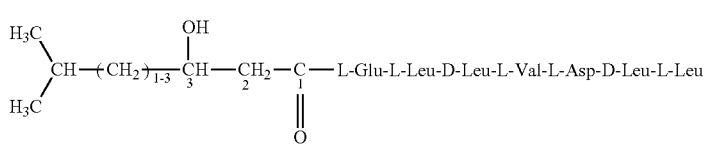

(SEQ. ID. NO. 1)

(VI)

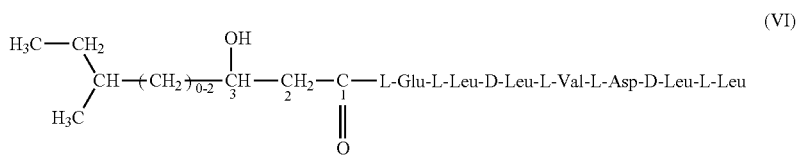

(SEQ. ID. NO. 6)

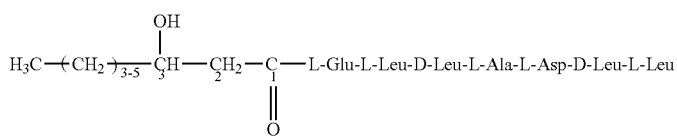

(VII)

(SEQ. ID. NO. 6)

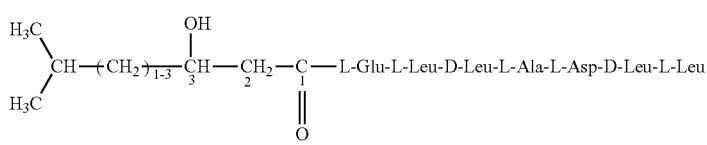

(VIII)

(SEQ. ID. NO.6)

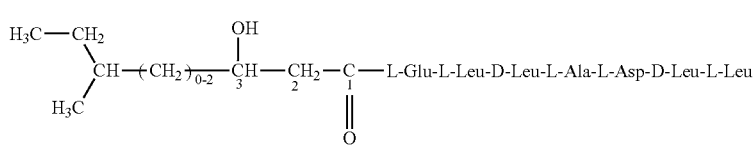

(IX)

FIG. 4 Formulae of linear analogues of surfactin with amino acid sequence L-Glu-L-Leu-D-Leu-L-Ala-L-Asp-D-Leu-L-Leu (SEQ. ID. NO. 6), in which the β-hydroxy fatty acid chain is composed of 7-9 atoms of C and which has a linear (VII), iso- (VIII) or anteiso- (IX) configuration.

Example 5

As in example 4, except that the column is placed in a microwave reactor.

Example 6

As in example 4, except that the column is placed in a magnetic field.

Example 7

Lipopeptides obtained by the method described in examples 1 to 6 were

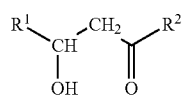

analysed by means of liquid chromatography and mass spectrometry. The structures of linear analogues of surfactin obtained by the presented method have the following form:

where:
$R^1$—alkyl group with the number of C≥4, and linear, iso- or anteiso-configuration;
$R^2$—a heptapeptide with chiral sequence LLDLLDL at the C-end, and amino acid sequence presented in the Table 1

TABLE 1

Amino acid sequence in group $R^2$ (heptapeptide) of linear analogues of surfactin.

| Sequence No. | 1 | 2 | 3 | 4 | 5 | 6 | 7 |
|---|---|---|---|---|---|---|---|
| SEQ. ID. NO. 1 | Glu | Leu | Leu | Val | Asp | Leu | Leu |
| SEQ. ID. NO. 2 | Glu | Leu | Leu | Val | Asp | Leu | Val |
| SEQ. ID. NO. 3 | Glu | Leu | Leu | Val | Asp | Leu | Ile |
| SEQ. ID. NO. 4 | Glu | Leu | Leu | Leu | Asp | Leu | Ile |
| SEQ. ID. NO. 5 | Glu | Leu | Leu | Leu | Asp | Leu | Val |
| SEQ. ID. NO. 6 | Glu | Leu | Leu | Ala | Asp | Leu | Leu |
| SEQ. ID. NO. 7 | Glu | Leu | Leu | Leu | Asp | Leu | Leu |
| SEQ. ID. NO. 8 | Glu | Leu | Leu | Ile | Asp | Leu | Leu |
| SEQ. ID. NO. 9 | Glu | Leu | Leu | Ile | Asp | Leu | Ile |
| SEQ. ID. NO. 10 | Glu | Ile | Leu | Ile | Asp | Leu | Ile |
| SEQ. ID. NO. 11 | Glu | Val | Leu | Val | Asp | Leu | Val |
| SEQ. ID. NO. 12 | Glu | Ile | Leu | Val | Asp | Leu | Val |
| SEQ. ID. NO. 13 | Glu | Ile | Leu | Val | Asp | Leu | Ile |
| SEQ. ID. NO. 14 | Gln | Leu | Leu | Val | Asp | Leu | Leu |
| SEQ. ID. NO. 15 | Gln | Leu | Leu | Val | Asp | Leu | Val |
| SEQ. ID. NO. 16 | Gln | Leu | Leu | Val | Asp | Leu | Ile |
| SEQ. ID. NO. 17 | Gln | Leu | Leu | Ala | Asp | Leu | Leu |
| SEQ. ID. NO. 18 | Gln | Leu | Leu | Ala | Asp | Leu | Val |
| SEQ. ID. NO. 19 | Gln | Leu | Leu | Ala | Asp | Leu | Ile |

The invention claimed is:

1. A method for lipopeptides, the method comprising the steps of:
   mixing an aqueous solution of cyclic lipopeptides with activated carbon, said cyclic lipopeptides having a peptide ring closed by a lactone bond, so as to form a suspension;
   adsorbing a portion of said cyclic lipopeptides on a surface of said activated carbon so as to form adsorbed cyclic lipopeptides;
   hydrolyzing another portion of said cyclic lipopeptides on said surface of said activated carbon so as to break said lactone bond and form linear lipopeptides at a percentage at least or above 83% of total lipopeptides in said suspension;
   separating said activated carbon from said suspension, wherein said activated carbon has a surface area above 600 m$^2$/g, and wherein said aqueous solution is basic and has a pH at or above 9.71; and
   harvesting said linear lipopeptides from said suspension.

2. The method of claim 1, wherein the step of mixing said aqueous solution with said activated carbon is comprised of at least one of the following steps:
   microwaving said aqueous solution and said activated carbon;
   applying a magnetic field to said aqueous solution and said activated carbon; and
   applying an electric current to said aqueous solution and said activated carbon.

3. The method of claim 1, wherein said aqueous solution is from a flow system.

4. The method of claim 1, wherein said activated carbon is granulated.

5. The method of claim 1, wherein the step of harvesting comprises the step of:
   separating said linear lipopeptides from said suspension.

6. The method of claim 1, wherein said linear lipopeptides have structures of the following chemical formulae:

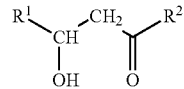

where:
   $R^1$—alkyl group with the number of C≥4, and linear, iso- or anteiso-configuration,
   $R^2$—a peptide terminated with a C-end of any sequence of amino acids and with a length of 4 to 12 amino acids.

7. The method of claim 1, wherein said aqueous solution is from a stationary system.

8. The method of claim 1, wherein said activated carbon is in the form of powder.

9. The method of claim 1, wherein said activated carbon is monolithic.

* * * * *